United States Patent
Glazer et al.

(10) Patent No.: US 8,278,053 B2
(45) Date of Patent: Oct. 2, 2012

(54) METHODS OF STUDYING A BIOMARKER, AND METHODS OF DETECTING A BIOMARKER

(75) Inventors: Gary M. Glazer, Los Altos, CA (US); Samira Guccione, Hillsborough, CA (US); Sanjiv S. Gambhir, Stanford, CA (US); Aloma L. D'Souza, Pacifica, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 561 days.

(21) Appl. No.: 12/467,586

(22) Filed: May 18, 2009

(65) Prior Publication Data
US 2010/0009400 A1    Jan. 14, 2010

Related U.S. Application Data

(60) Provisional application No. 61/054,257, filed on May 19, 2008.

(51) Int. Cl.
*C12Q 1/68* (2006.01)
*G01N 33/567* (2006.01)
*G01N 33/574* (2006.01)

(52) U.S. Cl. ............. 435/6.14; 435/7.21; 435/7.23; 435/4

(58) Field of Classification Search ............ None
See application file for complete search history.

(56) References Cited

U.S. PATENT DOCUMENTS

| 6,383,759 B1 * | 5/2002 | Murphy et al. ....... 435/7.1 |
| 6,589,173 B1 * | 7/2003 | Mitragotri ............ 600/437 |
| 2003/0064025 A1 * | 4/2003 | Yang et al. ............ 424/9.6 |

* cited by examiner

*Primary Examiner* — Chris R Tate
*Assistant Examiner* — Douglas F White
(74) *Attorney, Agent, or Firm* — Thomas, Kayden, Horstemeyer & Risley, LLP (57) ABSTRACT

Embodiments of the present disclosure provide for methods of studying (e.g., detecting, localizing, and/or quantifying) biomarker(s) and the like.

9 Claims, 8 Drawing Sheets

METHODS OF STUDYING A BIOMARKER, AND METHODS OF DETECTING A BIOMARKER

CROSS-REFERENCE TO RELATED APPLICATION

This application claims priority to U.S. provisional application entitled, "Methods of detecting biomarkers, and methods of amplifying and localizing biomarker detection," having Ser. No. 61/054,257, filed on May 19, 2008, which is entirely incorporated herein by reference.

STATEMENT REGARDING FEDERALLY SPONSORED RESEARCH OR DEVELOPMENT

This invention was made with government support under Grant No.: ICMIC P50 CA114747, from the National Cancer Institute. The government has certain rights in the invention.

BACKGROUND

Biomarkers are biological molecules that can be used as indicators of the physiologic state of a disease, as well as detectors for following changes during disease progression. Therefore, biomarkers can serve an important role in clinical medicine for detection (including early detection before the presence of clinical disease), diagnosis, treatment, monitoring, risk, and prognosis of diseases. With the completion of the initial draft of the human genome and the rapid growth in high throughput assays, the race for discovery of biological markers has begun.

Two significant limitations of biomarkers include the following. First, they are present in low concentrations and difficult to discriminate from noise. Second, most biomarkers are detected in compartments remote from their origin so that the location of the site producing the biomarker is occult (e.g., the biomarker of primary prostate cancer, PSA, is produced in the prostate but is generally detected in the blood). Once the prostate cancer spreads and PSA is elevated, the blood biomarker does not reveal the site of disease spread which has produced the PSA).

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 6(a) and 6(b) are graphs that illustrate the effects of cell death on CEA release in cultured cell line LS174T.

SUMMARY

Embodiments of the present disclosure provide for methods of studying (e.g., detecting, localizing, and/or quantifying) biomarker(s) and the like. In an embodiment of a method of releasing a biomarker, among others, the method includes using an external energy from a source to perturb a spatially localized area of a tissue to release one or more biomarkers from the tissue into a fluid.

In other embodiments, the method may include one or more of the following: detecting one or more of the following: the presence of the one or more biomarkers in the fluid, the concentration of the one or more biomarkers in the fluid, or both the presence and the concentration of the one or more biomarkers in the fluid; comparing the detected one or more biomarkers to the components in the fluid prior to the perturbation of the spatially localized area of a tissue; determining if the one or more biomarkers was present in the fluid prior to the perturbation of the spatially localized area of a tissue by comparing the detected biomarkers in the fluid before and after the perturbation of the spatially localized area of a tissue; determining if the concentration of the one or more biomarkers changed after perturbation by comparing the concentration of the one or more biomarkers in the fluid before and after the perturbation of the spatially localized area of a tissue; and/or determining the tissue from which one or more biomarkers were released by comparing the detected biomarkers in the fluid before and after the perturbation of the spatially localized area of a tissue.

In another embodiment of a method of releasing a biomarker, among others, the method includes: using an external energy from a source to perturb a spatially localized area of a tissue to release one or more biomarkers from the tissue into a fluid; detecting one or more of the following: the presence of the one or more biomarkers in the fluid, the concentration of the one or more biomarkers in the fluid, or both the presence and the concentration of the one or more biomarkers in the fluid; comparing the detected one or more biomarkers to the components in the fluid prior to the perturbation of the spatially localized area of a tissue; and determining the tissue from which one or biomarkers were released by comparing the detected biomarkers in the fluid before and after the perturbation of the spatially localized area of the tissue.

DETAILED DESCRIPTION

Before the present disclosure is described in greater detail, it is to be understood that this invention is not limited to particular embodiments described, and the embodiment of the invention as such may, of course, vary. It is also to be understood that the terminology used herein is for the purpose of describing particular embodiments only, and is not intended to be limiting, because the scope of the present disclosure will be limited only by the appended claims.

Unless defined otherwise, all technical and scientific terms used herein have the same meaning as commonly understood by one of ordinary skill in the art to which this invention belongs.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of imaging, biochemistry, biology, molecular biology, and the like, which are within the skill of the art. Such techniques are explained fully in the literature.

The examples herein are put forth so as to provide those of ordinary skill in the art with an illustrative disclosure and description of how to perform the methods and use the compounds disclosed and claimed herein. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also contemplated that, where multi-step processes are described in the present disclosure that steps can be executed in different sequence where this is logically possible.

As used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

DEFINITIONS

In describing and claiming the disclosed subject matter, the following terminology will be used in accordance with the definitions set forth below.

As used herein, the term "host" or "organism" includes humans, mammals (e.g., cats, dogs, horses, etc.), living cells, and other living organisms. A living organism can be as simple as, for example, a single eukaryotic cell or as complex as a mammal. Typical hosts to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications. In some embodiments, a system includes a sample and a host.

The term "sample" can refer to a tissue sample, a cell sample, a fluid sample, and the like. The sample may be taken from a host. The tissue sample can include hair (including roots), buccal swabs, blood, saliva, semen, muscle, or from any internal organs. The term "sample" may refer to a fluid that can be selected from, but is not limited to, urine, blood, ascites, pleural fluid, spinal fluid, semen, other biological fluids (e.g., secretion from the breast (e.g., ductal fluid)), and the like. The body tissue can include, but is not limited to, skin, muscle, endometrial, uterine, and cervical tissue. It should be noted that samples in vitro are media samples from cells in culture.

The term "detectable" refers to the ability to detect a signal or presence of a biomarker over a background signal.

The term "detectable biomarker", "detectable signal", or the phrase "detection of a biomarker" refers to the detection (directly or indirectly) of a biomarker in a sample such as a fluid. The detection of a biomarker refers to the ability to detect and distinguish the presence of a biomarker in a sample from other background signals derived from the sample. In other words, there is a measurable and statistically significant difference (e.g., a statistically significant difference is enough of a difference to distinguish among the acoustic detectable signal and the background, such as about 0.1%, 1%, 3%, 5%, 10%, 15%, 20%, 25%, 30%, or 40% or more difference between the detectable signal and the background) between detectable signal and the background. Standards and/or calibration curves can be used to determine the relative intensity of the detectable signal and/or the background. The detectable signal can be generated from small to large concentration of a biomarker. In an embodiment, the detectable signal may need to be the sum of each of the individual biomarker compounds. In an embodiment, the detectable signal can be generated from a summation, an integration, or other mathematical process, formula, or algorithm. In an embodiment, the summation, the integration, or other mathematical process, formula, or algorithm can be used to process the detectable signal so that the detectable signal can be distinguished from background noise and the like.

The term "perturb" or "perturbation" refers to the shaking, vibration, movement, sonication, and/or modification of subcomponents of the tissue such as the membranes of the nucleus and cytoplasm.

The term "tissue" refers to muscle tissue (e.g., striated, smooth, and cardiac), connective tissue (e.g., bone, tendons, ligaments, vessels, cartilage, muscle sheath, linings, vascular tissue, blood, lymph, and the like), nervous tissue (e.g., nerve cells, glial cells, and the like), and epithelial tissue (e.g., skin, mucosa, serosa, and the like). One or more types of tissue can form an organ. Embodiments of the present disclosure include perturbing a tissue, which may also include perturbing a part of or the entire organ. In an embodiment, the term "tissue" includes muscle tissue, connective tissue, nervous tissue, and epithelial tissue, with the proviso that the tissue does not include the brain, the spine, the lung, the bowels, and tissue within bone. In an embodiment where the perturbation is caused by ultrasound, the term "tissue" includes muscle tissue, connective tissue, nervous tissue, epithelial tissue, and a combination thereof, with the proviso that the tissue does not include the brain, the spine, the lung, the bowels, and tissue within bone.

GENERAL DISCUSSION

Embodiments of the present disclosure include methods of studying (e.g., detecting, localizing, and/or quantifying) one or more biomarkers and the like. Embodiments of the present disclosure can be used to both amplify and localize the site of production of the one or more biomarkers, which may overcome one or more of the limitations mentioned above. In an embodiment, the method includes a minimally invasive technique using external energy from a source to perturb a tissue so that the biomarker(s) is released from the tissue into a fluid (e.g., blood). A spatially localized area of the tissue can be perturbed or a larger area of the tissue(s) (e.g., large tissue or a part of or an entire organ) can be perturbed depending on factors such as tissue type, tissue size, the fluid, and the like. Subsequently, the fluid (e.g., the fluid that contacts the tissue directly or indirectly) can be tested using an assay (e.g., proteomic, genomic, or the like) or other technique to determine the presence, the concentration, and/or the type of biomarker(s) present in the fluid. The results obtained from the fluid can be correlated to the biomarker(s) present in the perturbed tissue. It should be noted that embodiments of the present disclosure contemplate that the perturbation of the tissue could reduce the number (types of biomarkers), amount (concentration) of biomarker(s) released, and the like, and such information could be useful for the analysis and/or evaluation.

An advantage of the present disclosure includes the ability to perturb a spatially localized area of the tissue, so that the source of the biomarker is more accurate. Another advantage of embodiments of the present disclosure includes increasing the concentration of the biomarker in the fluid (relative to the levels of biomarkers in the fluid prior to perturbation) so that the biomarker can be detected over the background signal. In other words, embodiments of the present disclosure amplify (in relative terms to the other components or the components prior to perturbation) the biomarker(s) to increase the signal to noise ratio. In an embodiment, the presence of the biomarker, biomarker concentration, number of different types of biomarkers, and the like, can be tested prior to and after perturbation of the tissue. Thus, the presence, type, or the like, of the biomarker(s) can be correlated with the perturbation of the spatially localized area of the tissue. Another advantage of an embodiment of the present disclosure includes the ability to detect unknown biomarkers since the signal to noise ratio of the detection of the biomarkers increases. In other words, biomarkers that may have been present but could not be detected because their presence is lost in the noise associated with the detection of the biomarker can be detected using embodiments of the present disclosure. The fluid after perturbation is transformed relative to the fluid prior to perturbation since the fluid after perturbation can have new biomarkers present, changes in the concentration of the biomarker, combinations thereof, and the like.

Embodiments of the present disclosure enable more reliable and reproducible results for determining the presence, concentration, and/or type of one or more biomarkers as compared to currently used techniques. By perturbing a spatially localized area of the tissue using an external energy, determination of the presence of the biomarker, the concentration of the biomarker, and/or the type of biomarker(s), are more reliable as a result of an increase of the signal to noise ratio of the analysis. In addition, the source of the biomarker (s) is more reliable since the perturbation is on a spatially localized area of the tissue. As noted above, detection of biomarker(s) can be conducted prior to and after the perturbation on a spatially localized area of the tissue so that the source of the biomarker(s) is known. In other words, the fluid can be tested and/or analyzed prior to perturbation of the localized area to establish a background. Then, perturbing a spatially localized area of the tissue can be conducted and the fluid can be tested and/or analyzed and compared with the background signal to determine the presence of the biomarker, the concentration of the biomarker, and/or the type of biomarker(s). It should be noted that the background can be established before or after (as long as a reasonable amount of time has passed so the levels can recover to the base line) the perturbation. Thus, the accuracy and ability to detect biomarkers in a fluid (and tissue) is enhanced.

In an embodiment, the biomarker(s) can be monitored periodically over a time period (e.g., minutes, hours, days, months, or more) to characterize the time dynamics of the change in the concentration of the biomarker(s). For example, a spatially localized area of the tissue can be perturbed using an external energy (e.g., ultrasound) at a time, to. Subsequently, the fluid can be tested and/or analyzed. At a time, $t_1$ (e.g., minutes, hours, days, months, or more) the spatially localized area of the tissue can be perturbed again, and the fluid can be tested and/or analyzed. The various data points can be compared to one another and/or to base line data obtained before and/or after (without perturbation). Additional data points at one or more times (e.g., $t_2, t_3, t_4, t_n \ldots t_{n+1}$) to produce a time dynamics picture, which can be analyzed and studied to determine any patterns or the like. The results can be used to provide a diagnosis or prescribe a way forward for the patient.

Embodiments of the present disclosure can be conducted on living hosts (e.g., humans, animals, and the like) since the perturbation is minimally invasive (e.g., using an ultrasound system to generate the external energy) and the collection of the fluid is minimally invasive (e.g., collection of blood, urine, and the like). After collecting the fluid sample, an analysis can be conducted on the fluid in regard to the biomarkers.

Embodiments of the present disclosure can be used for the detection (including early detection before the presence of clinical disease), diagnosis, treatment, monitoring, and/or prognosis of one or more diseases. In this regard, embodiments of the present disclosure can be used to perturb a spatially localized area of the tissue using an external energy to cause the release of a biomarker(s) from the tissue into a fluid, for example release of the biomarker into a fluid of a living host. The biomarker(s) may have direct access to the fluid or may flow to the fluid indirectly. Subsequently, the fluid is tested and/or analyzed for the presence of the biomarker(s), concentration of the biomarker(s), identity of the biomarker(s), and the like. Thus, the presence of the biomarker(s) can be correlated to the spatially localized area of the tissue, which enables the detection, diagnosis, treatment, monitoring, and/or prognosis of one or more diseases or conditions (e.g., cancer, tumors, and the like).

In an embodiment, methods of the present disclosure can be used to study cancerous cells, precancerous cells, cancer, and/or tumors. For example, the presence of one or more biomarkers can be used to study the cancerous cells, precancerous cells, cancer, and/or tumors and could provide insight into the appropriate diagnosis and/or treatment. In an embodiment, other diseases and/or conditions can be studied by detecting the presence of a biomarker(s), concentration of the biomarker(s), and/or the type(s) of biomarker(s).

In an embodiment, the tissue can be perturbed using an external energy generated by a source such as, but not limited to, an ultrasound system, an electromagnetic radiation system (e.g., where the electromagnetic radiation covers the entire physical spectrum), and combinations thereof. In an embodiment, the source is an ultrasound system. Although not intending to be bound by theory, the external energy perturbs (e.g., shakes, vibrates, or the like) the tissue and causes biomarkers to be released or movement of the biomarker from the tissue to the fluid. For example, the external energy increases the movement of the biomarker through the cell membranes as well as increases the vascular permeability of the area of the tissue perturbed so that the biomarkers or portions thereof can enter the fluid (e.g., extracellular fluid, lymphatics, blood, or the like) of the host.

The spatial localization of an area of the tissue can be conducted using an anatomical/molecular imaging system such as, but not limited to, a positron emission tomography (PET) system, a single photon emission computed tomography (SPECT) system, a magnetic resonance imaging (MRI) system, a computed tomography (CT), a photoacoustic, an optical bioluminescence and/or a fluorescence system, an ultrasound system, or combinations thereof. The perturbing external energy, for example with ultrasound, can be shaped (focused) so that it can affect all or only part of the tissue from which biomarkers are desired to be released providing added localization of the biomarker. In this way, different parts of tissue, tumor, and/or organ can be interrogated for biomarkers.

The biomarkers can include, but are not limited to, Alpha-fetoprotein (AFP) (e.g., Nonseminomatous germ cell tumor monitoring, Cirrhosis with liver mass (Hepatocellular Carcinoma)), and the like), Cancer Antigen 27.29 (CA 27.29) (e.g., Stage II or III Breast Cancer Monitoring), Cancer Antigen 19-9 (CA 19-9) (e.g., Specific pancreatic mass evaluation), Cancer Antigen 125 (CA 125), (e.g., Postmenopausal pelvic mass evaluation, Ovarian Cancer monitoring, and the like), Carcinoembryonic Antigen (CEA) (e.g., Stage II or III Colorectal Cancer monitoring), Human Chorionic Gonadotropin-beta subunit (bHCG) (e.g., Nonseminomatous germ cell tumor monitoring, Choriocarcinoma diagnosis and monitoring, and the like), Microglobulin-beta 2 subunit (b2-M) (e.g., Multiple Myeloma diagnosis and monitoring), and Prostate Specific Antigen (PSA) (e.g., Prostate Cancer screening and monitoring, Adenocarcinoma in men with unknown primary, and the like). It should be noted that embodiments of the present disclosure can be used to detect previously unknown biomarkers as well. In an embodiment, the biomarkers could also include non-protein biomarkers such as microRNA, DNA, RNA, small molecules, and the like. In an embodiment, the biomarkers could also potentially include whole cancer cells or parts thereof.

In an embodiment, the fluid can be analyzed using one or more techniques (an assay (e.g., proteomic, genomic, circulating cell, or the like) or other technique) that can be used, to determine the presence of one or more biomarker(s), the concentration of the biomarker(s), and/or the type of biomarker(s) present in the fluid, which can be correlated to the perturbed tissue. Embodiments of the present disclosure can use assays such as, but not limited to, ELISA's, mass spectrometry, genomic/proteomic nanosensors, PCR, microfluidic platforms for cell/protein separation, magnetic strategies, and the like, and combinations thereof. Once the biomarker(s) are analyzed and/or tested, biomarker(s) present in the perturbed tissue can be studied and/or analyzed.

EXAMPLES

Now having described the embodiments of present disclosure, in general, the examples describe some additional embodiments of the present disclosure. While embodiments of present disclosure are described in connection with the examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

The earlier detection of cancer may be facilitated by the detection of biomarkers which circulate in the bloodstream. Problems with the use of serum biomarkers to detect cancer include their low concentration and the lack of spatial localization of the origin of the biomarker. In this disclosure, we determined that ultrasonography, by likely altering permeability of the cell membranes of tumors, allowed the release of tumor biomarkers into the extracellular milieu. This effect both amplified and spatially localized the signals emanating from serum biomarkers. Tests were conducted both in cell culture and in living mice.

Materials/Methods: The colon cancer cell line LS174T that produces a well-studied biomarker; carcinoembryonic antigen (CEA), was used. CEA levels were measured both before and after application of ultrasonography to the tumor. Low frequency (1 MHz) ultrasound was applied to cultured cells and to subcutaneous tumors of the cells implanted into nude mice. The released CEA was detected in culture media or murine submandibular blood samples using an enzyme-linked immunosorbant assay Cell death due to the treatment was also studied.

Results: Application of 1 MHz (10% duty cycle. 30 sec) ultrasound pulses to cells, in culture, at increasing power levels (0, 0.1, 0.3, 0.5 W/cm$^2$) showed an increase in CEA levels in the media, with <1% cell death. Increased CEA release was also observed with cell culture treatments at constant power level (0.3 Wcm$^2$; 1 MHz; 10% duty cycle) and an increase in time (1, 10, 20, 30 min). This increase was significant at 20 (p=0.03) and 30 (p=0.05) minutes. Subcutaneous tumors (n=6/group) subject to varying energy levels (0, 480, 600, 720 J) at 1 MHz, showed an increase in CEA concentration in blood with increase in energy (p=0.04). At 720 J, the increase in CEA levels was the highest (p=0.027) when compared to pre-treatment values.

Conclusion: We have developed a novel way to both amplify and spatially localize the signals from tumor biomarkers in blood. These methods moves us one step closer towards unification of the fields of in vitro and in vivo diagnostics.

Example 2

Materials/Methods

Figure 1:
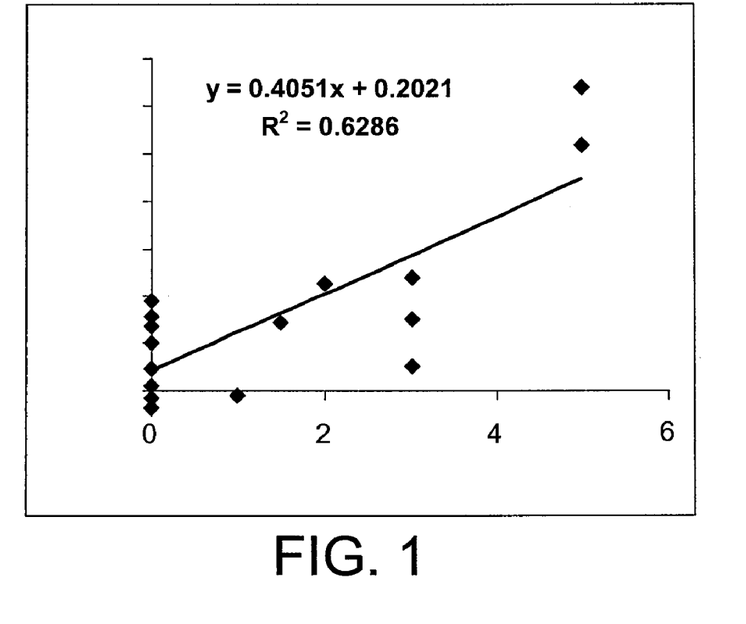
FIG. 1 is a graph that shows the increase in CEA with an increase in cell death.
Figure 2:
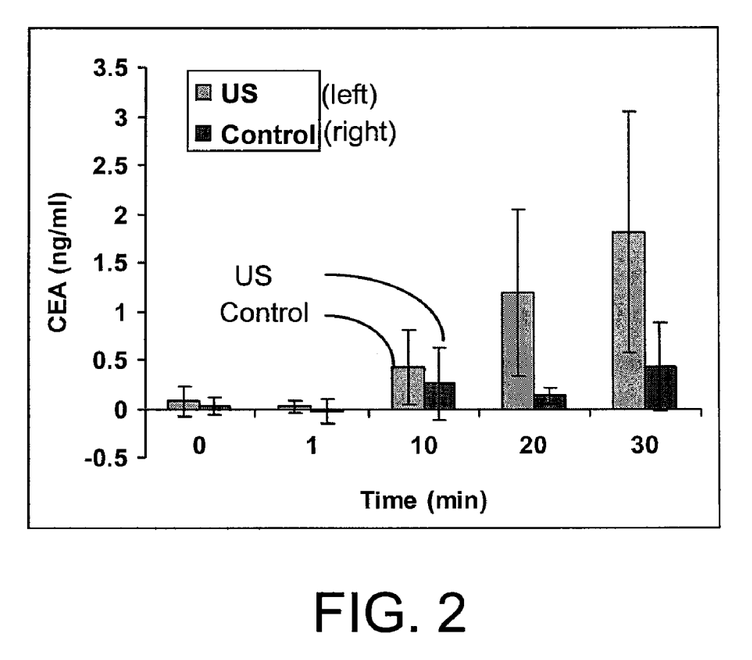
FIG. 2 is a graph that shows the variation in time, constant ultrasound power, and CEA concentration.
Figure 3A:
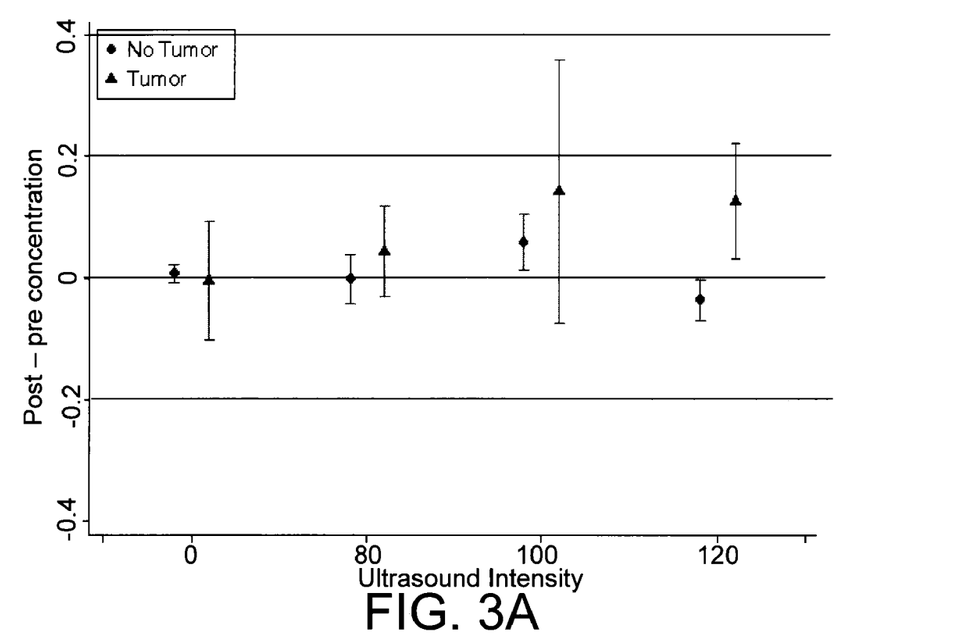
FIG. 3A illustrates a graph describing data about mice with (n=6/treatment) or without tumors that were exposed to six minutes of ultrasound at intensity levels of 0, 80, 100, or 120.
Figure 3B:
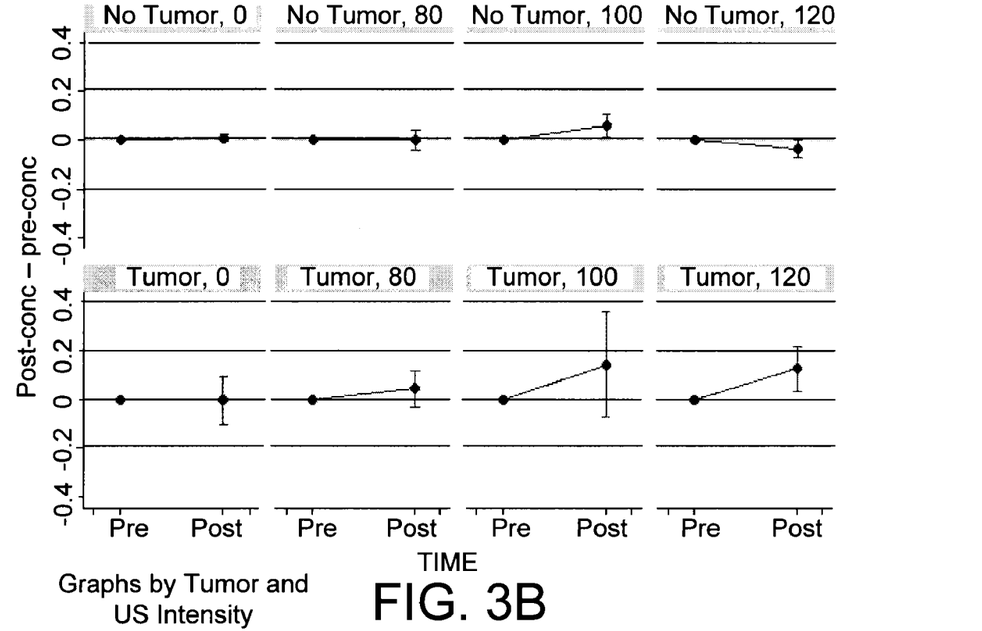
FIG. 3B illustrates a graph describing data of blood samples that were collected before (pre) and immediately after (post) ultrasound treatments and the levels of CEA were determined using the ELISA.
Figure 4:
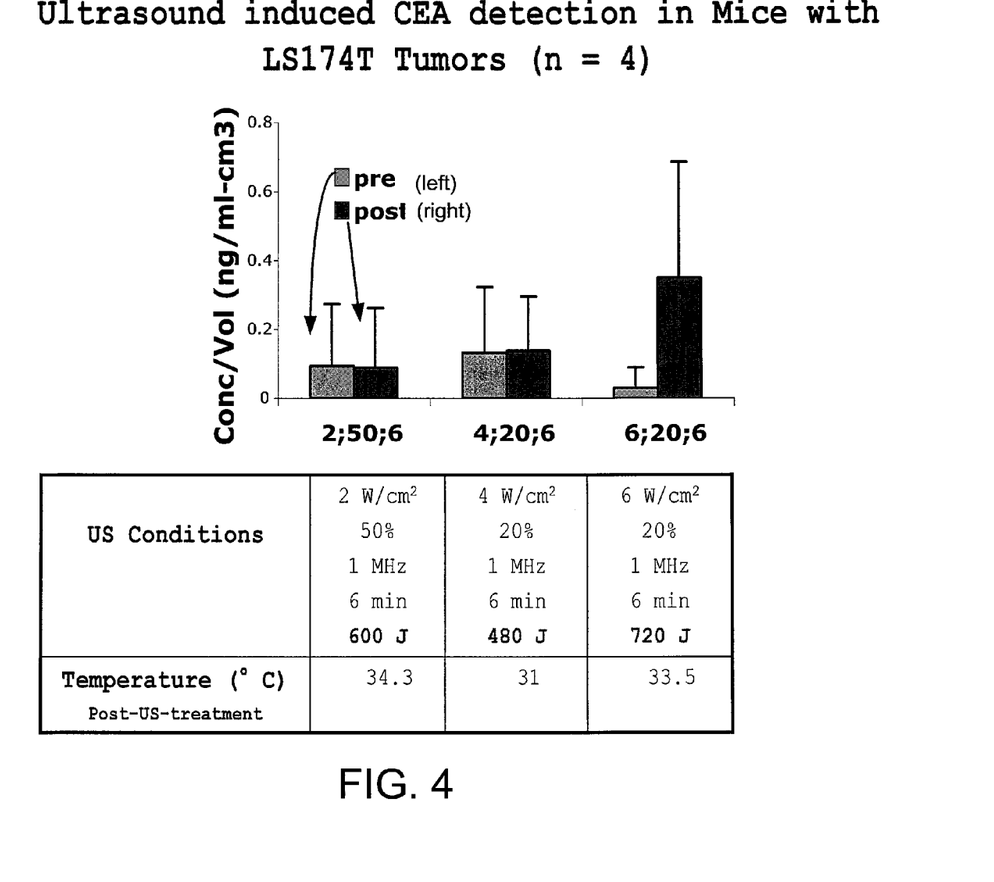
FIG. 4 illustrates ultrasound induced CEA detection in mice with LS174T tumors (n=4).
Figure 5:
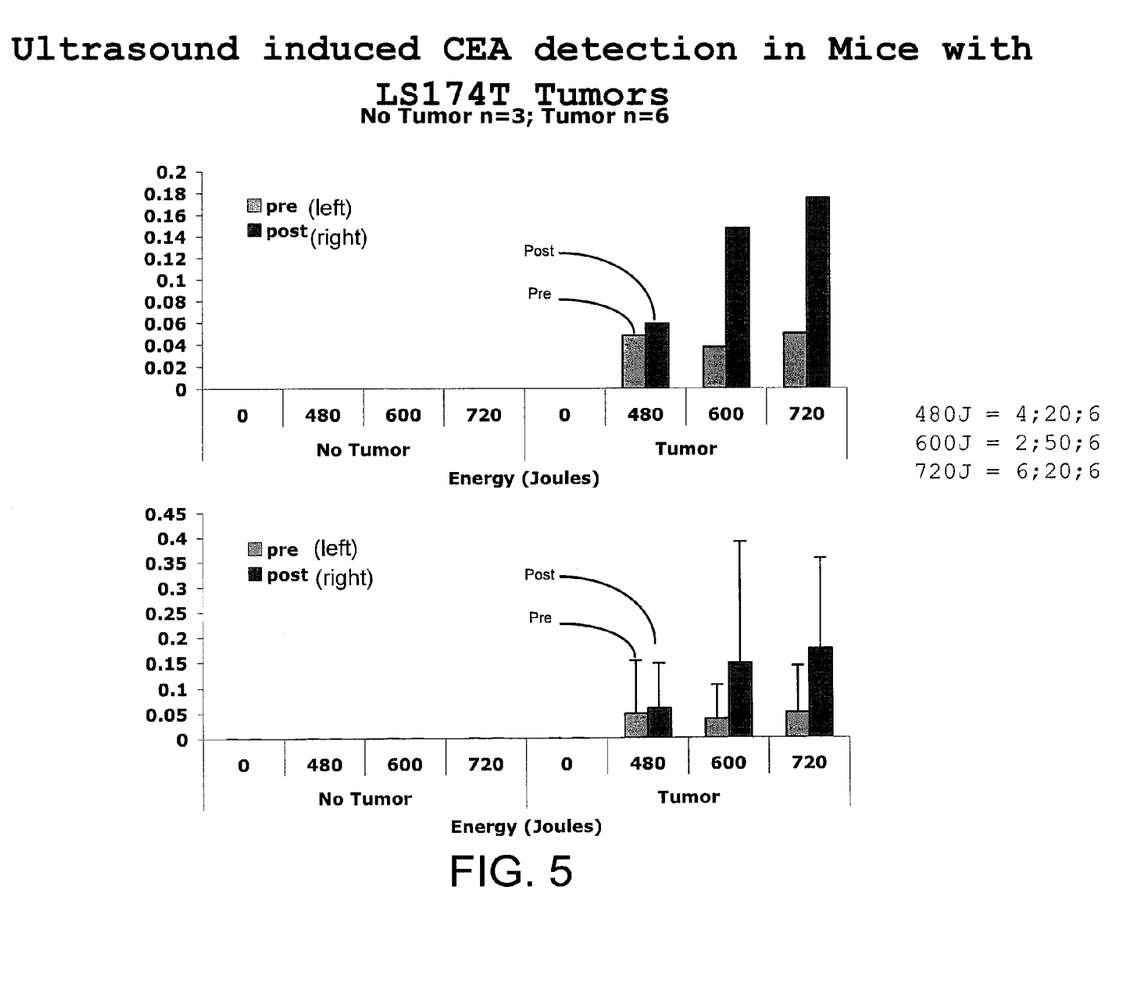
FIG. 5 illustrates ultrasound induced CEA detection in mice with LS174T tumors (no tumor n=3, and tumor n=6).

Materials
Cell Lines:
Colon cancer cell line, LS174T, was obtained from the American Type Culture Collection (Catalog number: CL-188).
U/S Apparatus
Ultrasound was produced using the Sonitron 2000, from Rich-Mar Corp.
ELISA
CEA was detected using an ELISA kit obtained from United Biotech, Inc. (CM-201).
Mice
Nude mice (nu/nu) were obtained from Charles Rivers Laboratories, Inc. The mice used were female, 6 to 8 weeks old. They were housed at the Stanford Research Animal Facility.
Serum Collection
Plasma was collected using plasma separator tubes with Lithium Heparin from BD Biosciences (Catalog number: 365958)
Methods
Cell Culture
LS174T cells were cultured in Dulbecco's Modified Eagle's Media: Nutrient mix F-12 complete media (Gibco 11330), supplemented with 10% fetal bovine serum (Gibco 26140).
CEA Detection
CEA concentrations were determined using an Enzyme Linked Immunosorbant Assay (ELISA) kit from United Biotech, Inc.
U/S Treatment on Cell Lines
LS174T cells were seeded at 1.5×10$^6$ cells in 6-well tissue culture plates and grown overnight in complete media. The next day the media was removed and the cells rinsed with media. 2 mls/well of fresh media was added to the cells immediately before the exposure of the cells to the ultrasound. The cells were exposed to ultrasound using the 21.5 mm transducer of the Sonitron 2000 (Rich-Mar, Corp.), from the bottom of the plate. Ultrasound coupling gel (Parker Laboratories, Inc.) was used to ensure a good connection between the transducer and the plate. Media samples were collected at various time points and analyzed for CEA concentration using an Enzyme Linked Immunosorbant Assay (ELISA) kit from United Biotech, Inc. Control and ultrasound-treated samples were run in parallel in separate plates. Cell death was determined using Trypan blue staining of the cells.
Mice and U/S Treatment
Female nude mice (nu/nu, Charles Rivers) were implanted subcutaneously with 10×10$^6$ LS174T cells. The tumors were grown for two weeks or until the size was greater than 0.5 cm$^3$. The mice were anesthetized with 2% Isofluorane in oxygen and kept on a heating pad during treatment. Ultrasound was applied using the 21.5 cm$^3$ transducer (Sonitron 2000—Rich-Mar, Corp.) at varying conditions. Blood samples were collected, by a submandibular bleed, immediately prior and after the ultrasound treatment and the separated plasma analyzed for CEA concentrations by the ELISA (United Biotech, Inc.).
Results
Invitro-LS174T-CEA
FIG. 1 is a graph that shows the increase in CEA with an increase in cell death. An increase in the power levels of the ultrasound caused an increase in cell death. The cell death showed a linear correlation (R=0.628) to the amount of CEA detected. In order to determine CEA levels not due to cell death, the cell death was kept to <3%, which involved keeping the power levels to less than or equal to 0.5 W/cm$^2$, in vitro.
FIG. 2 is a graph that shows the variation in time, constant power and CEA concentration. At a constant power level of 0.5 W/cm$^2$ (n=8) and increase in time, the CEA levels in the media showed an increase with time. In comparison with the control un-treated samples, using similar conditions, the ultrasound-treated samples showed a significant increase in CEA levels at 20 (p<0.03) and 30 (p<0.05) minutes. Cell death as determined by Trypan blue staining was below 3% at the various time points.
Mice with (n=6/treatment) or without tumors were exposed to six minutes of ultrasound at intensity levels of 0, 80, 100 or 120 (FIG. 3A). Blood samples were collected before (pre) and immediately after (post) ultrasound treatments and the levels of CEA were determined using the ELISA (FIG. 3B). There was significant interaction between ultrasound intensity and tumors at the highest intensities (p<0.039, linear regression of post concentration and tumor). At the intensity of 120 there was significance between the pre and post-treatment CEA levels in the blood (p<0.003, Wilocoxon test). Robust standard errors were used to account for within-animal correlations. Ultrasound treatments on a non-tumor area in mice with tumors, showed no change in post blood CEA level compared to pre-treatment levels.
FIG. 4 illustrates ultrasound induced CEA detection in Mice with LS174T tumors (n=4).
FIG. 5 illustrates ultrasound induced CEA detection in Mice with LS174T tumors (no tumor n=3, and tumor n=6).

Example 3

Brief Introduction

Blood biomarkers have significant potential applications in early detection and management of various diseases including cancer. Most biomarkers are present in low concentrations in blood and are difficult to discriminate from noise. Furthermore, blood measurements of a biomarker do not provide information about the location(s) where it is produced. This example describes a novel strategy to increase the concentration of biomarkers in blood as well as localize the source of biomarker signal using ultrasound energy directly applied to tumor cells. We test and validate this strategy in cell culture experiments and mouse tumor xenograft models using the human colon cancer cell line, LS174T, while measuring the biomarker, carcinoembryonic antigen (CEA), before and after the use of ultrasound to liberate the biomarker from the tumor cells. The results demonstrate that the application of low frequency ultrasound to tumor cells causes a significant release of tumor biomarker, which can be measured in the blood. Furthermore, we establish that this release is specific to the direct application of the ultrasound to the tumor, enabling a method for localization of biomarker production. This example shows that it is possible to use ultrasound to amplify and localize the source of CEA levels in blood of tumor-bearing mice and will allow for a new way to more accurately determine the presence and localization of disease using a relatively simple and noninvasive strategy.

Introduction

Blood biomarkers have the potential to significantly impact clinical medicine because they can potentially predict risk of disease; signal the initial presence of disease and its recurrence; help in the selection of patients for a particular treatment; and monitor response during and after treatment. Consequently, there has been a large body of work attempting to discover and validate serum biomarkers, particularly for the detection of cancers (1-10). Despite the numerous investigations exploring the clinical use of biomarkers and a large increase in the number of potential biomarkers identified, few novel blood biomarkers are used for clinical care, and their rate of introduction into the clinical environment is actually falling (8, 11). Additionally, the reproducibility of studies using blood biomarkers for the detection of cancer has been poor (4, 12).

Two fundamental problems hinder current serum biomarker research: the concentration of biomarker signal in the blood is often very low, and the localization of the site(s) of origin of the biomarker signal cannot be determined solely from measurement of blood levels of the biomarker. The most desirable biomarkers are produced within a specific tissue but are present in extremely low concentrations in the plasma. The concentrations in plasma are often so low that biomarker measurements can either be difficult or impossible to differentiate from the noise of the measurement process and system. This markedly hinders the efficacy and reliability of biomarker measurement in blood. Furthermore, even when a disease-specific (e.g., tumor) biomarker can be reliably identified by its presence in the blood, there is no information about its specific anatomic site of origin or spatial localization. So, in the hypothetical case of a newly identified serum biomarker that reliably detects a cancer, the patient and his/her physician might be dealing with information about the presence of a tumor without knowing precisely where it is located in the body.

This example describes that both of these fundamental issues could be addressed by applying ultrasonic energy to potential tumor sites. Ultrasound with frequencies 20 kHz to 16 MHz has been shown to reversibly compromise the integrity of cell membranes causing an increase in permeability, which has been widely used as a method of intracellular delivery of macromolecules (13-18). The precise mechanism of this action is not clear, but it has been shown to cause the formation of transient pores due to membrane disruption (15, 19, 20). Because multiple copies of biomarker proteins are present either on the surface of tumor cells, within cell membranes, or within the cytoplasm of these cells, it is possible that these copies can be released from tumor cells by the appropriate application of ultrasonic energy to the tumor, potentially providing biomarker amplification in the extracellular space fluid or in blood. The strategy is also based on the fact that ultrasonic energy can be deposited in a spatially localized way, potentially releasing biomarkers only when the energy is applied to a tumor or portions of a tumor. We chose the first biomarker used for routine clinical cancer care in the detection and recurrence of colon cancer, CEA (2, 21), to test our strategy, at a low, 1 MHz, frequency of ultrasonic energy. Our results in cell culture and in tumor-bearing living mice form the basis of this proof-of-concept report.

Results

Figure 6:
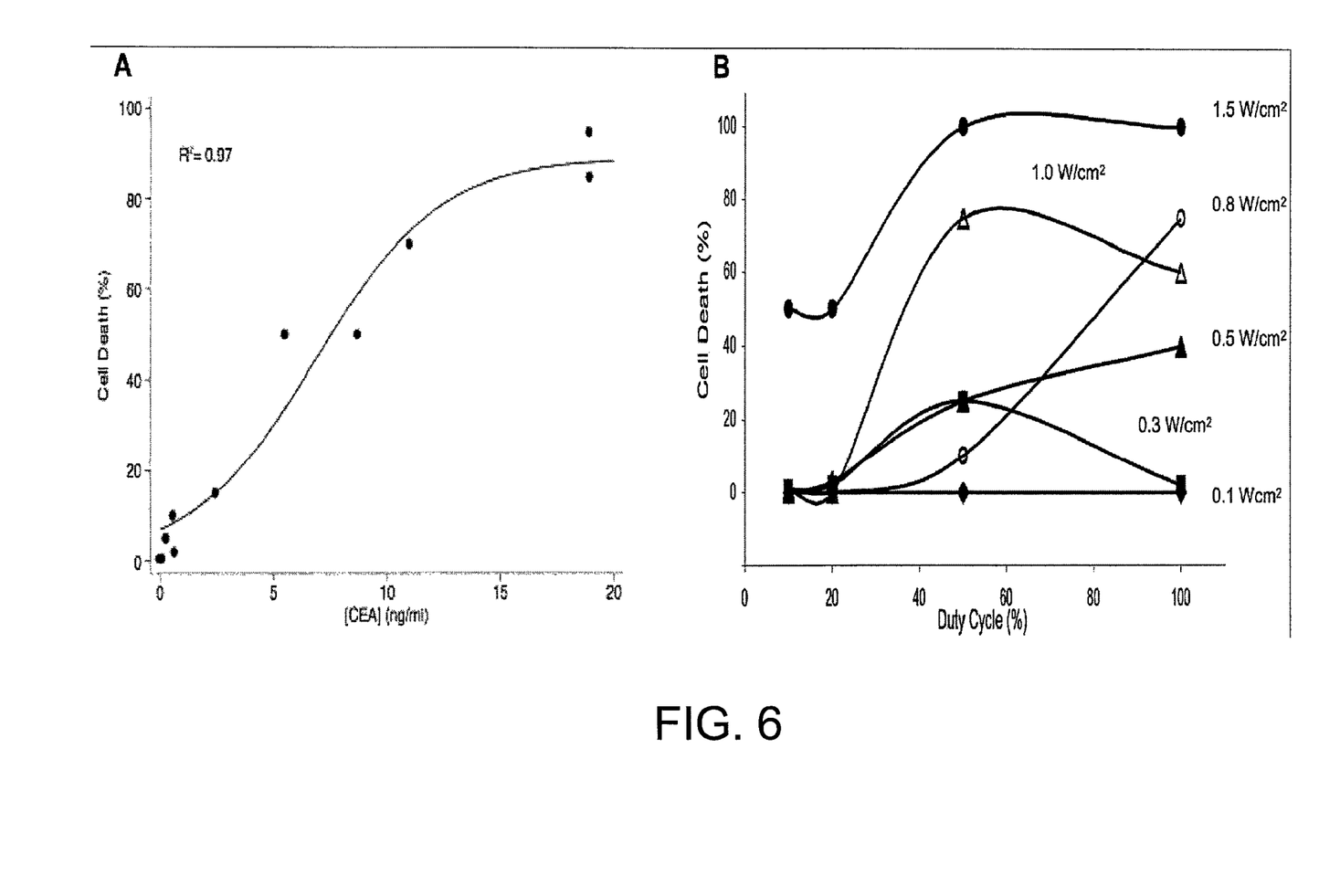
FIG. 6(a) is a graph that shows the correlation of cell death and CEA levels released due to varying ultrasound conditions. Cell death, visualized by Trypan blue staining, correlated with the levels of CEA detected in the media using the ELISA. Correlation: $R^2=0.97$ (three-parameter logistic function).
FIG. 6(b) is a graph that shows that LS174T cells were exposed to ultrasound at various power levels (0.1, 0.3, 0.5, 0.8, 1.0, 1.5 W/cm$^2$) at 10, 20, 50, and 100% duty cycles. Cell death was determined using Trypan blue staining. There is, in general, increased cell death with increased power and duty cycle. Less than 1% cell death was observed at 10 and 20% duty cycle with all power levels lower than 1 W/cm$^2$.

Cell Culture Studies:

Effects of Cell Death on CEA Release:

LS174T cells were exposed to varying ultrasound intensities to study the correlation between CEA levels released in the media and the amount of cell death. CEA levels progressively increased with the percentage of cell death with a correlation of 0.97 (FIG. 6a). In order to ensure the CEA released from cells was not entirely due to cell death in our studies, we determined the ultrasound conditions for which we obtained less than 5% of total cell death. Cells were exposed to 1 MHz ultrasound frequency at various power levels (0.1, 0.3, 0.5, 0.8, 1.0, and 1.5 W/cm$^2$) and at different duty cycles (10, 20, 50, and 100%) for 30 seconds. Power is defined as the energy (W) emitted divided by the area (cm$^2$) of the emitting surface, and duty cycle is defined as the percent of the time the sound wave is delivered. The amount of cell death determined showed a relative increase with increase in power and duty cycle (FIG. 6b). At power levels below 1 W/cm$^2$ and duty cycle below 20%, the cell death in cell culture was estimated to be less than 1%. This result shows that a large amount of the detected CEA in media at high ultrasound power deposition is likely due to cell death. To test whether CEA release could be achieved at a low level of cell death, we subsequently used ultrasound at a low power level (0.3 W/cm$^2$) and at a short duty cycle (10%).

Figure 7:
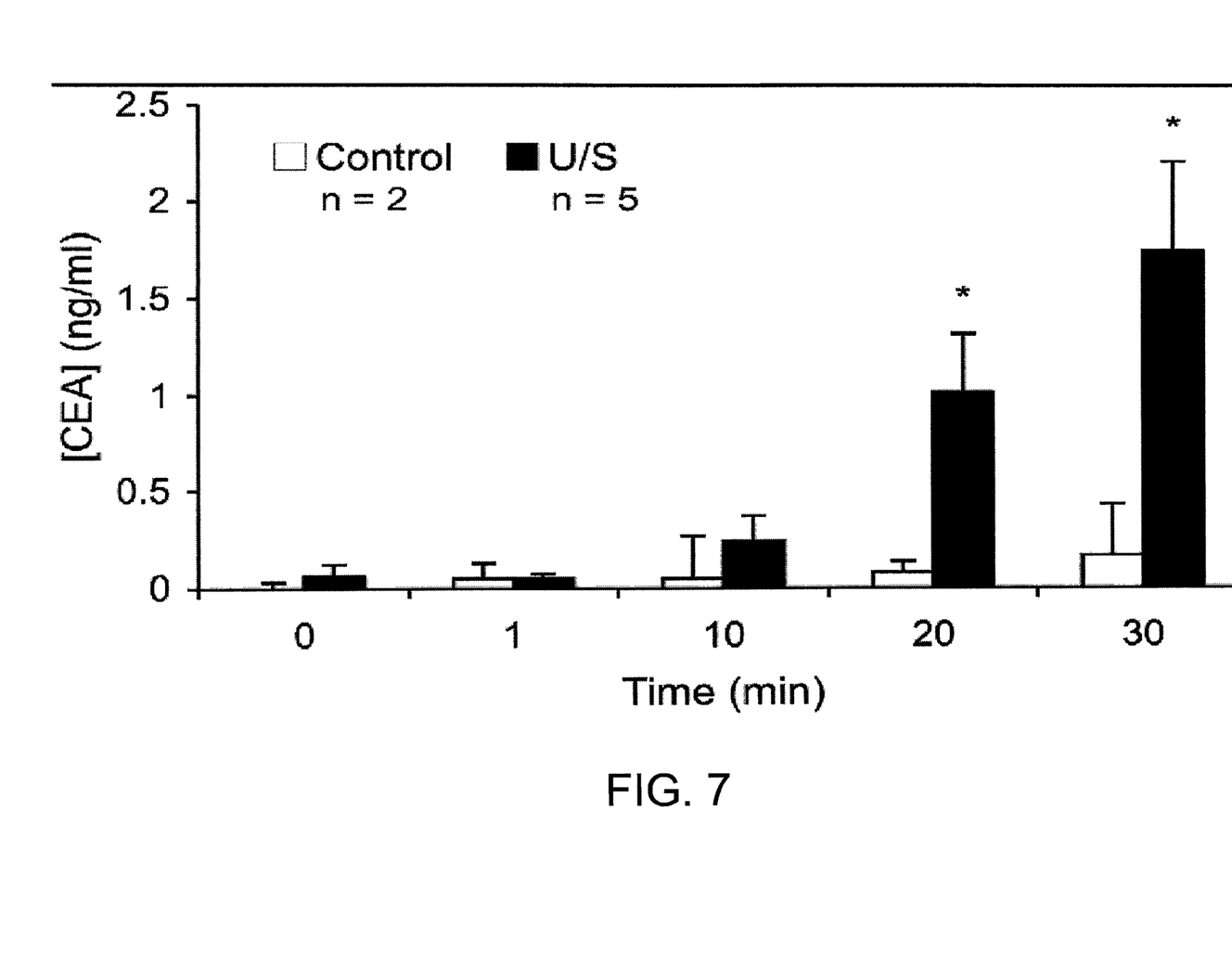
FIG. 7 is a graph that illustrates the time-release of CEA from cells in culture treated with ultrasound. LS174T cells in culture were exposed to a constant level of ultrasound (0.3 W/cm$^2$, 10% duty cycle, 1 MHz) for 0, 1, 10, 20, and 30 min. An increase in CEA levels was observed in the ultrasound-treated (U/S, n=5) media samples when compared to the non-treated control samples (Control, n=2). This 3- to 4-fold increase was significant at 20 and 30 min (*$P=0.036$) when compared to controls. Error bars shown are s.e.m.

Time-Release of CEA from Cells in Culture Treated with Ultrasound:

To study the release of CEA, cells were exposed to a constant ultrasonic pulse (1 MHz, 0.3 W/cm$^2$, 10% duty cycle) for 30 min (n=5). A steady accumulation of CEA in the media with time was observed (FIG. 7). Within 30 min, there was a three- to four-fold increase in the CEA levels when compared to untreated control samples (n=2) for the same time period. This increase in accumulation was significant in comparison with the controls at 20 and 30 min (both with P<0.036). Cell death across all the samples was below 4%. The results of this experiment were repeated and confirmed.

Living Mice Studies:

Release of CEA from Tumors Treated with Ultrasound:

In order to prove our hypothesis in living subjects, we used xenograft subcutaneous tumors of LS174T cells in nude mice (n=7 per treatment group). The clearance of CEA from blood in nude mice has been previously well studied. Human CEA extracted from tumors shows a clearance in nude mice of about 90% within 10 min, 95% by 30 min, and 98% by two hours; whereas CEA extracted from human serum has a clearance of 2.5 hours when injected in nude mice (22). In accord with the above results, which we confirmed, all treatments and blood collections were done within 10-15 min after the initial energy deposition.

Figure 8:
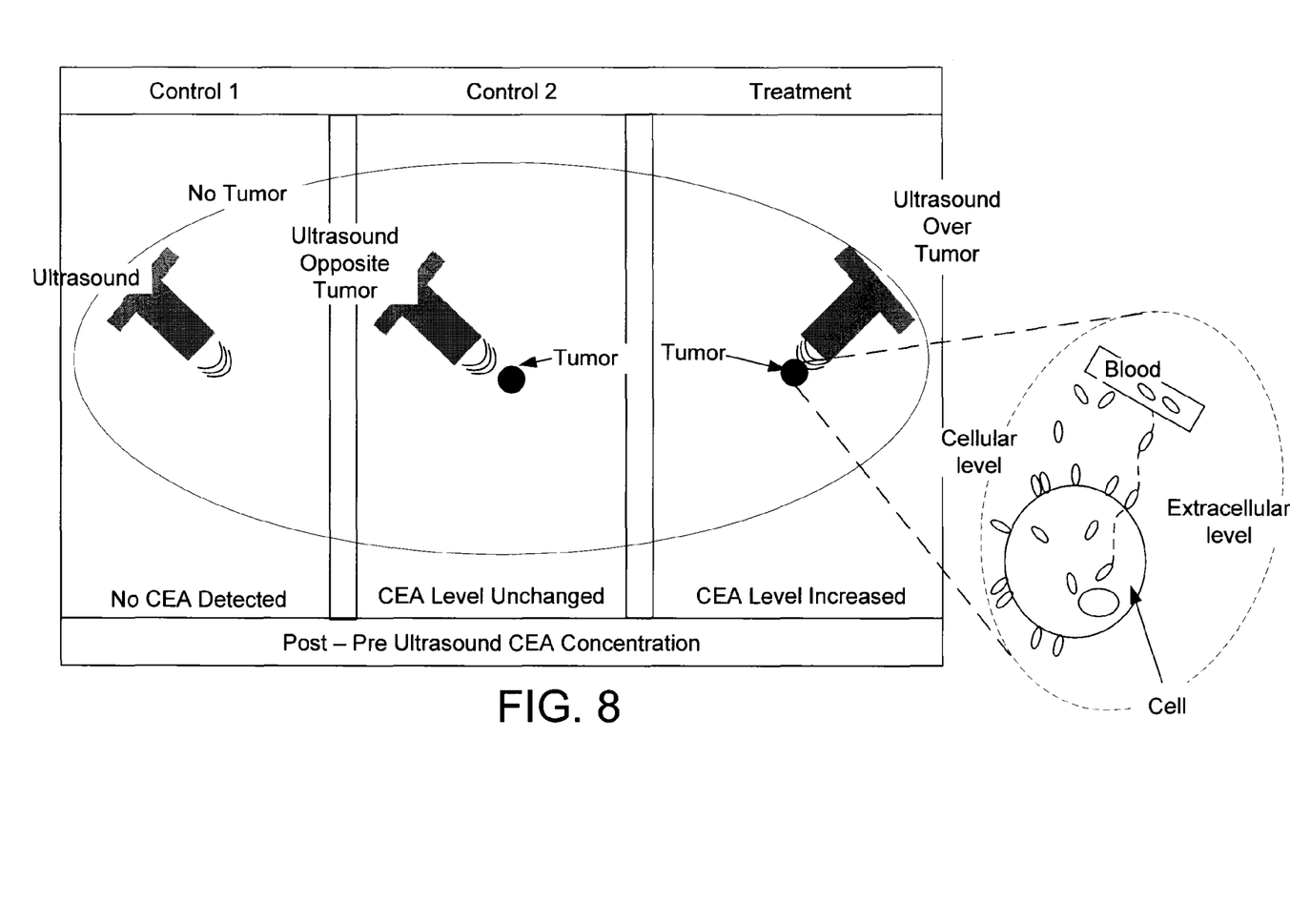
FIG. 8 illustrates a schematic setup of ultrasound treatment in living mice. Studies in living mice were done in three groups. Control 1: Ultrasound was applied to mice with no tumors. Control 2: Ultrasound was applied to a non-tumor-bearing region of mice with tumors. Treatment: Ultrasound was applied directly to the site of the tumor. Post-minus pre-treatment levels of CEA were hypothesized to increase in the treatment group due to the release of CEA into the blood stream from the tumor.
Figure 9:
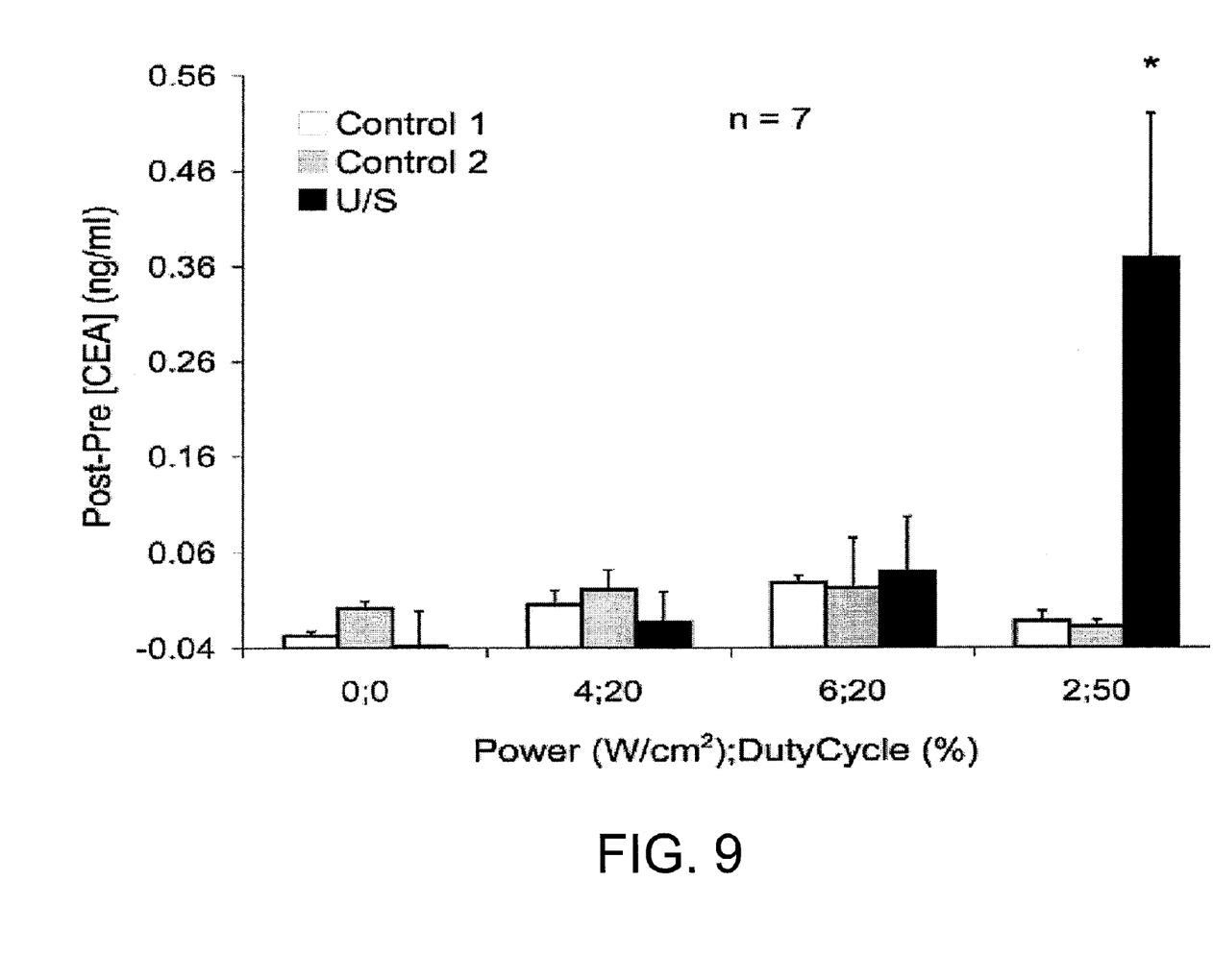
FIG. 9 illustrates a graph showing the release of CEA from tumors treated with ultrasound. Subcutaneous LS174T tumors (n=7 per group) exposed to 6 min of ultrasound at 0, 4, and 6 W/cm$^2$ at 20% duty cycle did not show a significant increase in the CEA levels with increase in power ($P<0.81$ and 0.99, respectively). At 2 W/cm$^2$ at 50% duty cycle for 6 min, there was a significant increase in the CEA release when compared to Control 1 or Control 2 (* both with $P<0.031$). The Controls 1 and 2 did not show any significant increase in CEA release ($P<0.689$ and 0.538, respectively). Error bars shown are s.e.m.

Four ultrasound treatments were undertaken at 1 MHz for 6 min: no power or 0 W/cm$^2$; 4 W/cm$^2$ at 20% duty cycle; 6 W/cm$^2$ at 20% duty cycle; and 2 W/cm$^2$ at 50% duty cycle. Before implantation of the cells, the mice were treated with ultrasound as their own internal "no-tumor" controls (FIG. 8, Control 1). As a further control, the ultrasound-treatment was done on the tumor-bearing mice on a non-tumor-bearing site (flank opposite to tumor implantation) after implantation and growth of the tumors (FIG. 8, Control 2). Both these controls showed no significant change in the levels of CEA in blood with the ultrasound treatments (P<0.689 and 0.538, respectively), and there was no significant difference between the two controls (FIG. 9, P<0.183). For the treatment group, ultrasound was applied directly to the site of the tumor with the ultrasound transducer positioned over the subcutaneous tumor (FIG. 9). The 21.5 mm transducer used has a well-collimated beam of energy, which penetrates tissue to a depth of 10-15 mm and measures about 11 mm across (Sonitron 2000, Rich-Mar, Corp.), allowing for most of the tumor to be exposed to the energy.

At 20% duty cycle, which from the cell culture experiments would not be expected to cause much cell death or optimal CEA release, the use of power of 6 $W/cm^2$ and 4 $W/cm^2$ did not show significant increase in CEA-release when compared to their controls (FIG. 9, P<0.81 and 0.99, respectively). To see if an increase in the duty cycle would cause a substantial release of CEA, 2 $W/cm^2$ at 50% duty cycle for 6 min was used and showed a significant increase in CEA levels after ultrasound treatment when compared with Control 1 and Control 2 (both with P<0.03) (FIG. 9). Preliminary experiments done with higher power levels at 50% duty cycle caused superficial burns on the skin and were not pursued.

Cell death due to ultrasound treatment in the subcutaneous tumors was not easily studied. Areas of necrosis were present in most tumor sections and ultrasound-induced necrosis was not clearly differentiable from tumor necrosis. Sections stained for apoptosis, using caspase-3 staining, showed no marked differences in the area positively stained within the total area when comparing the 0 $W/cm^2$ (0.89% of total area) to tumors that had a positive release of CEA at 2 $W/cm^2$ (0.51% of total area) (n=5 fields per tumor section, n=7 tumors per treatment group). Overall, the caspase-3 stained cells were less than 2% of the area of the tumor sections (4 $W/cm^2$=0.83% and 6 $W/cm^2$=1.78% of total area).

Discussion:

Both the cell culture and living mice results presented here support the idea that ultrasonic energy applied to tumors can release protein biomarkers from the tumor, amplifying biomarker signals measured outside of the cells. In the live mouse, enough biomarker was released into the bloodstream to provide signal amplification so that blood levels of the biomarker were significantly elevated beyond baseline measurements. Also, the example has shown in mice that additional signal from the tumor-specific biomarker CEA was released only when ultrasonic energy was deposited in the tumor and was not released when the energy was deposited in normal tissue remote from the tumor. Thus, ultrasonic energy appropriately targeted and deposited in macroscopic tumors can potentially obviate major current limitations of serum biomarkers by providing a way for both the amplification of the biomarker signal and localization of the site of biomarker residence.

There are a number of clinical applications that could be pursued given the results of our study. One very common problem in clinical practice is the detection of a lesion that is incidentally found on CT or MR imaging studies performed for another purpose (23). In patients with existing malignancies, these "incidentalomas" commonly require further study, biopsy, or even surgical removal. The technique we describe could potentially be used in patients whose malignancies harbor biomarkers to distinguish between metastatic disease (which would release biomarker) and benign, incidental lesions such as adenomas. Another clinical application that could be readily pursued is the characterization of a dominant lesion, for example in the breast, as benign or malignant. Our findings also have the potential to be used for proof of disease recurrence in patients who have tumors that produce biomarkers and who have a soft tissue mass on CT or MR studies. In fact, patients like these could potentially have a low intensity image-guided ultrasound study to prove disease recurrence followed by a high intensity focused ultrasound treatment to ablate the lesion.

While there are many potential clinical applications enabled by embodiments of the present disclosure, there are four main considerations to our study that deserve further comment. These considerations involve the use of a single biomarker; the use of subcutaneous, macroscopic tumors; the use of a species-specific model; and the application and optimization of US energy deposition. It should be noted that we used a single biomarker (the protein CEA) for these proof-of-principle studies. For example, the plasma half-life in nude mice of human-serum extracted CEA is 2.5 hours (22), which is favorable for our study because the CEA released by our intervention was measured and detected before it was markedly degraded by proteases and cleared from the circulation. Methods of Example 1 may need to be altered for other proteins with short plasma half-lives. This is because longer-half lives for a given biomarker would mean even a longer time interval prior to the need for drawing blood from the subject. However, we would expect that methods of the disclosure can be used with biomarkers with long half lives as well as with those with short plasma half lives under appropriate conditions. Another consideration in the use of CEA is that there are a large number of CEA copies per tumor cell ($10^5$-$10^6$ per tumor cell (24)); other potential tumor cell biomarkers may have far fewer copies per cell, thus minimizing their amplification potential. But even at low concentrations, the methods should provide some amplification. With improved detection technologies, smaller increases in the fluid of interest (e.g., blood) will likely be detectable. Also, we did not extensively study the biophysics of the ultrasonic intervention, so we are not certain whether most of the amplified signal came from the cell surface or from the cytoplasm of the cells that received energy deposition. This might be a consideration for biomarkers that are disproportionately located in one cellular site. However, embodiments of the present disclosure can be used to amplify the biomarkers that may be disposed deeper in the cytoplasm, which may be an added advantage of using embodiments of the present disclosure.

In the clinical environment, a single plasma biomarker may not prove effective for the detection or management of disease and multiple panels of biomarkers will be required (2, 7-9). This seems to be based on the fundamental biomarker problems our study addresses, and we are uncertain about how this issue will unfold in the future. Despite differences related to plasma half-lives and copy numbers, we believe it will be possible to amplify and localize signals from multiple biomarkers that reside within, or on, the surface of cells, which may likely overcome the potential problems described above.

Differences in the accessibility of biomarkers to blood once they are released also affect the results of insonification. For a biomarker to be measured in the blood, it needs to be released from the tissue of origin and find access to the bloodstream. Results of biomarker release from the subcutaneous tumor experimental model we used may not be directly generalizable to the more common situations of tumors that develop within the soft tissues of organs in living systems. It is known that the microvasculature environment between the two can be different, and this may cause differential access of released biomarkers to the bloodstream. For example, orthotopic tumor models are known to have a higher macromolecular vascular permeability than subcutaneous tumors, which would allow for a greater access of the biomarker to the blood (25, 26). Also, although the work in living mice reached clear statistical significance when appropriate ultrasound energy was used, it was more variable than the cell culture experiments. One major source of variability was that the number of viable tumor cells after tumor implantation and development was likely significantly different in each of the mice, and, thus, the amount of biomarker available for amplification differed among animals. However, despite these issues, embodiments of the present disclosure were used to amplify the biomarkers.

Another consideration of our study is that we insonicated macroscopic tumors, and we have no evidence the method could be applied to tumors that are smaller and earlier in their state of evolution. However, we believe embodiments of the present disclosure can be applied to smaller tumors because detection technologies for biomarker release in blood are rapidly improving and would allow even smaller amounts of released biomarkers from smaller tumors to be detected. Microscopic tumors that cannot be imaged in vivo would be particularly problematic and, thus, might not be amenable to our technique. However, it is possible that our method could be applied to an area that appears morphologically normal by imaging but that releases biomarkers, permitting the detection of disease that has not yet become macroscopic. For example, a possible scenario for its application includes a patient with high-risk for cancer having a baseline blood draw for biomarker measurements and then having a repeat blood draw after deposition of ultrasound energy in an area of possible tumor (e.g., breast). In this way, the patient's own pre-ultrasound biomarker level is compared to the post-ultrasound level, allowing potentially higher discriminatory capacity and spatial localization of possible tumor. If no tumor were present in the site of interest then no significant blood biomarker increase would be detected. This study would build on our mathematical modeling of early cancer detection through blood biomarker levels (10), as it allows for each patient to be his or her own control, pre- and post-ultrasound treatment.

The mouse is a useful model to prove the feasibility of our approach; whether the results can be generalized to other species, including humans, may be uncertain. However, we are confident that the general concept of biomarker amplification post-insonication will remain valid because the energy applied can penetrate to deeper tissues as needed, there are already treatment systems for applying ultrasound energy in humans for a different purpose (e.g., high-intensity frequency ultrasound (HIFU)). However, the measurement of biomarker release may be affected by differences among species regarding proteases, which degrade biomarkers at varying rates in the blood, as well as by differences in blood volume between species. We have recently started to mathematically model some of these issues to relate blood biomarker levels to tumor volume (10). For example, the blood volume of the mouse is small compared to humans. Post-insonication, biomarkers released from cells would be far more diluted in humans than in mice, and, thus, changes in biomarker concentration might be undetectable post-insonication. However, focused ultrasound systems, which differ and are improved compared to the ultrasound system we used, have been optimized for humans recently (27-30) and should provide signal amplification (and localization). Also, improvements in the signal detection of the biomarker by techniques such as mass spectroscopy and nanosensors should prove helpful in obviating this limitation (7). Thus, we expect embodiments of this disclosure to work in humans and provide valuable information, such as detecting new biomarkers, detecting changes in the concentration of biomarkers, and the like, that can be used to evaluate tissue for disease or related conditions.

Furthermore, our research on the use of ultrasound to perturb tumors and amplify biomarker signals is dependent on the ultrasonic energy reaching the tumor. As a result, an "acoustic window" from the transducer to the tumor is used. Ultrasound is reflected at air-tissue interfaces due to differences in acoustic impedances. In addition, ultrasound is highly attenuated by bone. Therefore, regions of living systems that lack acoustic windows include the lung, or any lesion completely surrounded by air, as well as regions surrounded by thick cortical bone. Fortunately, acoustic windows can generally be found for nearly all regions except for the brain, spine, lung, bowel, and within bone, so the method we propose has relatively few limitations due to the absence of acoustic windows for insonication. However, other perturbation techniques could be used to examine the brain, spine, lung, bowel, and within bone.

Also, we did not study how much of the released CEA came from live cells as opposed to cells that may have been killed because of the application of ultrasonic energy. The cell culture work clearly showed that cells killed by the deposition of ultrasound energy released very large amounts of CEA. This may be considered because in the clinical environment there would be little objection to killing tumor cells with ultrasound, and in this scenario we can expect large signal amplification that might permit signal detection in blood. For our work in living mice, we elected to deposit relatively smaller amounts of energy to minimize cell death yet achieve signal amplification. This balancing of cell death and signal amplification will need to be worked out for clinical application of our technique. However, we would expect embodiments of the present disclosure to work under appropriate conditions in humans and provide valuable information, such as detecting new biomarkers, detecting changes in the concentration of biomarkers, and the like, that can be used to evaluate tissue for disease or related conditions.

A major source of variability in vivo was due to the specifics of the ultrasound application. Ultrasonic energy was manually applied by placing the transducer over the tumor; however, the ultrasonic coupling to the surface was less than optimal due to the application of a rigid, flat transducer surface to a curved area of the tumor and of the animal. This introduced considerable variability into the results. The focal zone of the ultrasound energy deposition was not shapeable, but it was delivered uniformly through the tissue to a depth of a few centimeters; this could be considered to be suboptimal compared to what can be achieved with better ultrasound instrumentation. Thus, embodiments of the present disclosure may provide even better results than obtained in these experiments. In addition, it is contemplated that embodiments of the present disclosure could lead to even better results with biomarker detection technologies that can detect much smaller changes than possible with the ELISA.

Although we did not perform an extensive optimization of the energy deposition specifics in terms of the length of energy application or the intensity of the energy used and its correlation with biomarker amplification, many of these considerations could be overcome with the use of clinically available equipment that has been called "focused ultrasound" using image-guided MR thermometry (27-29). This equipment is available in many academic departments of radiology throughout the world. Using this equipment, precise amounts of ultrasonic energy can be deposited at specific locations within an MRI-visible tumor, and MR thermometry can measure in nearly real time the temperature of the tissues insonicated. In this way, specific locations of tissue can be altered in a graded way using ultrasonic energy with feedback during the experiment from image-localized temperature readouts. Thus, we expect that embodiments of the present disclosure to provide valuable information.

We envision a fairly clear pathway to explore clinical application of ultrasound for biomarker localization and release. Image-guided focused ultrasound has been used for the past decade to ablate tumors in humans, and so many of the potential pitfalls of using ultrasound to deposit energy locally in patients have already been overcome. In fact, the United States Food and Drug Administration granted approval of MR-guided focused ultrasound to treat uterine fibroids in 2004 (31). Since that time, thousands of patients have been treated using this technology for tumors, including those of the uterus, breast, brain, and metastatic disease of the bone (27, 32, 33). These treatments, which use high energy ultrasound, have proven quite safe with adverse events being quite uncommon (31). We do not anticipate significant safety concerns for the application of ultrasound to release biomarkers since considerably lower energy will be used than in applications to ablate tumors. Furthermore, because MR-guided focused ultrasound systems are already commercially available, there should be little delay in adapting system use to include spatially localized biomarker release.

In conclusion, we have proved the principle, that targeted ultrasonic deposition of energy to tumors can amplify biomarker signals in the blood as well as identify the biomarker release site. Consequently, our research directly addresses the current limitations of biomarker work, which include the difficulty in separating biomarker signal from noise and the inability to spatially localize the source of biomarker signal. The technique we have described should prove useful in humans to identify biomarkers in a visible lesion by appropriate application of ultrasonic energy and measurement of biomarker levels pre- and post-insonication.

Methods:

Cell Culture

The colon cancer cell line, LS174T (American Type Culture Collection), was cultured in Dulbecco's Modified Eagle's Media: Nutrient mix F-12 complete media (Gibco 11330), supplemented with 10% fetal bovine serum (Gibco 26140).

CEA Quantification

CEA concentrations in media or plasma samples were determined using an Enzyme Linked Immunosorbant Assay (ELISA) from United Biotech, Inc. (Catalog no. CM-201). Because the concentration of CEA in the plasma of the mice was at the lower end of the provided standard curve (1.5-30 ng/ml) of the kit, the standard curve was modified by dilution of the lowest standard to allow for a more reliable curve fit at the expected lower concentrations (0.047, 0.09, 0.19, 0.38, 0.75 ng/ml). The sensitivity of this assay was 0.05 ng/ml.

Ultrasound Treatment of Cells

LS174T cells were seeded at $1.5 \times 10^6$ cells in 6-well tissue culture plates (BD Biosciences, 35-3046) and grown overnight in complete media forming a 100% confluent monolayer of cells. The next day the media was removed, the cells were rinsed with media, and fresh media was added to the cells immediately before the ultrasound exposure. The cells were exposed to ultrasound using a 21.5 mm transducer of the Sonitron 2000 (Rich-Mar, Corp.) from the bottom of the plate. Ultrasound coupling gel (Aquasonic 100, Parker Laboratories, Inc.) was used to ensure a good contact between the transducer and the plate, with the transducer flushed against the plate. Media samples were collected and analyzed for CEA concentration by the ELISA. Control and ultrasound-treated samples were run in parallel in separate plates. Cell death was determined using Trypan blue (Invitrogen Co-op.). The media was removed and 100 µl of Trypan blue was added to the well. Live cells exclude the high molecular weight dye, and dead cells with disrupted cell membranes take in the dye and stain blue. The percent of dead cells was determined by counting the cells using a microscope.

Ultrasound Treatment of Mouse Models

Female nude mice (nu/nu, Charles Rivers Laboratories, Inc.), 6- to 8-weeks old, were subcutaneously implanted in the right flank area with $10 \times 10^6$ LS174T cells in 0.1 ml phosphate buffered saline, pH 7.4, using a 28G1/2 needle. The tumors were grown for approximately two weeks until the majority of the tumors were above 0.3 cm$^3$ in volume. The mice were anesthetized with 2% isoflurane in oxygen and kept on a heating pad during the treatment. Ultrasound was applied using the 21.5 mm transducer (Sonitron 2000, Rich-Mar, Corp.). Ultrasound coupling gel (Aquasonic 100, Parker Laboratories, Inc.) was used between the transducer and the skin. Submandibular blood samples (34) were collected using plasma separator tubes (BD Biosciences, catalog no. 36-5958), immediately prior (pre-treatment) and after (post-treatment) the ultrasound treatment. The volume of blood collected was approximately 75 µl per sample. No more than 10% of the blood volume of the mouse was collected per week, and 200 µl of warm saline was given subcutaneously to compensate for the loss of fluid. The separated plasma was analyzed for CEA concentrations by the ELISA. The change between pre- and post-concentration levels was used for comparison of CEA increases.

Controls included ultrasound treatments with blood analysis on the mice before tumor implantation (Control 1) and on the non-tumor-bearing region (left flank) of tumor-bearing mice (Control 2). The individual animal served as its own control.

The tumors from the mice were excised a day after the experiment, processed, and paraffin embedded. Sections cut through the center of the tumors were stained with hematoxylin (stains nuclei acids) and eosin (stains proteins) and immunostained for the apoptotic enzyme caspase-3 (Histo-Tec Laboratory). The tissue was visualized using the Axiovert 200M microscope (Carl Zeiss MicroImaging), and the percent of area stained for caspase-3 compared to the total area (n=5 fields per section) was determined using the Metamorph Imaging Series software, version 7.0.4 (Molecular Devices).

Statistical Analysis

Because of the difficulty of obtaining precise values at low concentration levels, nonparametric statistical methods robust to measurement imprecision were used. Biomarker levels as a function of cell death of cells in culture were fit with a three-parameter logistic growth function using nonlinear least squares. Progressive release of biomarkers under continuous ultrasound in culture was compared between treated and control samples by exact one-sided Wilcoxon tests done at each time point. For tumor release of biomarker under ultrasound, exact paired Wilcoxon tests on differences between pre- and post-ultrasound CEA concentrations were performed for tumor and non-tumor targets at each ultrasound level. Comparison of Control 1 to Control 2 was done with an exact two-sided paired Wilcoxon test stratified on ultrasound level. Statistical analyses were done with version 2.7.1 of the R system (www.r-project.org), using the "coin" package for conditional permutation inference from the CRAN archive (cran.r-project.org). All other statistical analyses were done with Stata Release 9.2 (Statacorp LLP, College Station, Tex.). A significance level of 0.05 was used.

References for Example 3, Each of which is Incorporated Herein by Reference:
1. Beachy S H & Repasky E A (2008) Using extracellular biomarkers for monitoring efficacy of therapeutics in cancer patients: an update. *Cancer Immunol Immunother* 57:759-775.
2. Chatterjee S K & Zetter B R (2005) Cancer biomarkers: knowing the present and predicting the future. *Future Oncol* 1:37-50.
3. Qiao M & Pardee A B (2007) Biomarkers, regerons, and pathways to lethal cancer. *J Cell Biochem* 102:1076-1086.
4. Ransohoff D F (2005) Bias as a threat to the validity of cancer molecular-marker research. *Nat Rev Cancer* 5:142-149.
5. Sawyers C L (2008) The cancer biomarker problem. *Nature* 452:548-552.
6. Mueller C, Muller B, & Perruchoud A P (2008) Biomarkers: past, present, and future. *Swiss Med Wkly* 138:225-229.
7. Hanash S M, Pitteri S J, & Faca V M (2008) Mining the plasma proteome for cancer biomarkers. *Nature* 452:571-579.
8. Gagnon A & Ye B (2008) Discovery and application of protein biomarkers for ovarian cancer. *Curr Opin Obstet Gynecol* 20:9-13.
9. Visintin I, et al. (2008) Diagnostic markers for early detection of ovarian cancer. *Clin Cancer Res* 14:1065-1072.
10. Lutz A M, Willmann J K, Cochran F V, Ray P, & Gambhir S S (2008) Cancer screening: a mathematical model relating secreted blood biomarker levels to tumor sizes. *PLoS Med* 5:e170.
11. Ransohoff D F (2007) How to improve reliability and efficiency of research about molecular markers: roles of phases, guidelines, and study design. *J Clin Epidemiol* 60:1205-1219.
12. Munkarah A, Chatterjee M, & Tainsky M A (2007) Update on ovarian cancer screening. *Curr Opin Obstet Gynecol* 19:22-26.
13. Chapman I V, MacNally N A, & Tucker S (1980) Ultrasound-induced changes in rates of influx and efflux of potassium ions in rat thymocytes in vitro. *Ultrasound Med Biol* 6:47-58.
14. Gambihler S, Delius M, & Ellwart J W (1994) Permeabilization of the plasma membrane of L1210 mouse leukemia cells using lithotripter shock waves. *J Membr Biol* 141:267-275.
15. Brayman A A, Coppage M L, Vaidya S, & Miller M W (1999) Transient poration and cell surface receptor removal from human lymphocytes in vitro by 1 MHz ultrasound. *Ultrasound Med Biol* 25:999-1008.
16. Mitragotri S, Blankschtein D, & Langer R (1995) Ultrasound-mediated transdermal protein delivery. *Science* 269:850-853.
17. Mitragotri S (2005) Healing sound: the use of ultrasound in drug delivery and other therapeutic applications. *Nat Rev Drug Discov* 4:255-260.
18. Schlicher R K, et al. (2006) Mechanism of intracellular delivery by acoustic cavitation. *Ultrasound Med Biol* 32:915-924.
19. Guzman H R, Nguyen D X, Khan S, & Prausnitz M R (2001) Ultrasound-mediated disruption of cell membranes. I. Quantification of molecular uptake and cell viability. *J Acoust Soc Am* 110:588-596.
20. Pitt W G, Husseini G A, & Staples B J (2004) Ultrasonic drug delivery—a general review. *Expert Opin Drug Deliv* 1:37-56.
21. Goldenberg D M, et al. (1981) CEA (carcinoembryonic antigen): its role as a marker in the management of cancer. *J Cancer Res Clin Oncol* 101:239-242.
22. Martin K W & Halpern S E (1984) Carcinoembryonic antigen production, secretion, and kinetics in BALB/c mice and a nude mouse-human tumor model. *Cancer Res* 44:5475-5481.
23. Thompson G B & Young W F, Jr. (2003) Adrenal incidentaloma. *Curr Opin Oncol* 15:84-90.
24. Shi Z R, Tsao D, & Kim Y S (1983) Subcellular distribution, synthesis, and release of carcinoembryonic antigen in cultured human colon adenocarcinoma cell lines. *Cancer Res* 43:4045-4049.
25. Hobbs S K, et al. (1998) Regulation of transport pathways in tumor vessels: role of tumor type and microenvironment. *Proc Natl Acad Sci USA* 95:4607-4612.
26. Fukumura D, Yuan F, Monsky W L, Chen Y, & Jain R K (1997) Effect of host microenvironment on the microcirculation of human colon adenocarcinoma. *Am J Pathol* 151:679-688.
27. Chapman A & ter Haar G (2007) Thermal ablation of uterine fibroids using MR-guided focused ultrasound—a truly non-invasive treatment modality. *Eur Radiol* 17:2505-2511.
28. Clement G T (2004) Perspectives in clinical uses of high-intensity focused ultrasound. *Ultrasonics* 42:1087-1093.
29. Kennedy J E (2005) High-intensity focused ultrasound in the treatment of solid tumours. *Nat Rev Cancer* 5:321-327.
30. Leslie T A & Kennedy J E (2007) High intensity focused ultrasound in the treatment of abdominal and gynaecological diseases. *Int J Hyperthermia* 23:173-182.
31. Hesley G K, Gorny K R, Henrichsen T L, Woodrum D A, & Brown D L (2008) A clinical review of focused ultrasound ablation with magnetic resonance guidance: an option for treating uterine fibroids. *Ultrasound Q* 24:131-139.
32. Kaiser W A, Pfleiderer S O, & Baltzer P A (2008) MRI-guided interventions of the breast. *J Magn Reson Imaging* 27:347-355.
33. Stewart E A, et al. (2003) Focused ultrasound treatment of uterine fibroid tumors: safety and feasibility of a noninvasive thermoablative technique. *Am J Obstet Gynecol* 189:48-54.
34. Golde W T, Gollobin P, & Rodriguez L L (2005) A rapid, simple, and humane method for submandibular bleeding of mice using a lancet. *Lab Anim* (NY) 34:39-43.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim the following:

1. A method of releasing and detecting a biomarker, comprising:
   perturbing a localized area of a tissue with an external energy source for a sufficient time to release one or more biomarkers from the tissue into a fluid, wherein the fluid is selected from the group consisting of: urine, blood, ascites, pleural fluid, spinal fluid, semen, ductal fluid, and a combination thereof;
   detecting one or more of the following: the presence of the one or more biomarkers in the fluid, the concentration of the one or more biomarkers in the fluid, or both the presence and the concentration of the one or more biomarkers in the fluid; and
   comparing the detected one or more biomarkers to those in the fluid prior to said perturbing.

2. The method of claim 1, further comprising:
   determining if the one or more biomarkers was present in the fluid prior to the perturbation of the spatially localized area of a tissue by comparing the detected biomarkers in the fluid before and after the perturbation of the spatially localized area of a tissue; and
   determining if the concentration of the one or more biomarkers changed after perturbation by comparing the concentration of one or more of the biomarkers in the fluid before and after the perturbation of the spatially localized area of a tissue.

3. The method of claim 1, wherein the source is an ultrasound source.

4. The method of claim 3, wherein the tissue is selected from the group consisting of: a muscle tissue, a connective tissue, a nervous tissue, an epithelial tissue, and a combination thereof, with the proviso that the tissue does not include the brain, the spine, the lung, the bowels, and tissue within bone.

5. The method of claim 1, further comprising:
   determining the tissue from which one or more biomarkers were released by comparing the detected biomarkers in the fluid before and after the perturbation of the spatially localized area of the tissue.

6. The method of claim 1, wherein the tissue is in a living host.

7. The method of claim 1, wherein the area of the tissue is spatially localized using an anatomic imaging system.

8. The method of claim 7, wherein the anatomic imaging system is selected from the group consisting of: a positron emission tomography (PET) system, a single photon emission computed tomography (SPECT) system, a magnetic resonance imaging (MRI) system, a computed tomography (CT), an optical bioluminescence and/or fluorescence system, an ultrasound system, and a combination thereof.

9. The method of claim 1, wherein the tissue is selected from the group consisting of: a precancerous tissue, a cancerous tissue, a tumor, and a combination thereof.

* * * * *